United States Patent
Liang et al.

(10) Patent No.: US 10,716,626 B2
(45) Date of Patent: Jul. 21, 2020

(54) METHOD AND SYSTEM FOR INTERACTIVE 3D SCOPE PLACEMENT AND MEASUREMENTS FOR KIDNEY STONE REMOVAL PROCEDURE

(71) Applicant: EDDA TECHNOLOGY, INC., Princeton, NJ (US)

(72) Inventors: Cheng-Chung Liang, West Windsor, NJ (US); Guo-Qing Wei, Plainsboro, NJ (US); Li Fan, Belle Mead, NJ (US); Xiaolan Zeng, Princeton, NJ (US); Jianzhong Qian, Princeton Junction, NJ (US)

(73) Assignee: EDDA TECHNOLOGY, INC., Princeton, NJ (US)

( * ) Notice: Subject to any disclaimer, the term of this patent is extended or adjusted under 35 U.S.C. 154(b) by 616 days.

(21) Appl. No.: 15/190,539

(22) Filed: Jun. 23, 2016

(65) Prior Publication Data

US 2016/0374760 A1    Dec. 29, 2016

Related U.S. Application Data

(60) Provisional application No. 62/183,998, filed on Jun. 24, 2015.

(51) Int. Cl.
*A61B 34/10* (2016.01)
*A61B 17/22* (2006.01)
*A61B 5/00* (2006.01)

(52) U.S. Cl.
CPC ............ *A61B 34/10* (2016.02); *A61B 5/4222* (2013.01); *A61B 5/7271* (2013.01);
(Continued)

(58) Field of Classification Search
CPC ..... A61B 1/307; A61B 5/0013; A61B 5/1076; A61B 5/4222; A61B 5/7271;
(Continued)

(56) References Cited

U.S. PATENT DOCUMENTS

| 8,311,303 B2* | 11/2012 | Suehling | G06K 9/6207 378/21 |
| 8,662,900 B2* | 3/2014 | Bell, III | G09B 23/28 434/262 |
| 2002/0077540 A1* | 6/2002 | Kienzle, III | A61F 2/4609 600/424 |
| 2002/0193800 A1* | 12/2002 | Kienzle, III | A61B 17/1703 606/80 |

(Continued)

OTHER PUBLICATIONS

International Preliminary Report on Patentability dated Jan. 4, 2018 International Search Report and Written Opinion dated Sep. 19, 2016 in International Application No. PCT/US2016/038951. in International Application No. PCT/US2016/038951.

*Primary Examiner* — Sae Won Yoon
(74) *Attorney, Agent, or Firm* — Pillsbury Winthrop Shaw Pittman LLP

(57) ABSTRACT

The present teaching relates to interactive medical image processing for surgical procedure planning. In one example, a three dimensional (3D) image of a kidney is obtained. The three dimensional image is rendered on a display screen. An input is received from a user specifying a location with respect to a representation of the kidney in the rendered three dimensional image. A representation of an instrument is rendered on the display screen based on the location. The instrument is automatically aligned with an infundibulum pathway of calyx at the location with respect to the kidney. A graphical line extension is rendered on the display screen to visualize the alignment of the instrument. One or more measurements related to the kidney are determined based on the location and an anatomical structure of the kidney.

22 Claims, 13 Drawing Sheets

(52) U.S. Cl.
CPC ...... *A61B 5/7435* (2013.01); *A61B 17/22004* (2013.01); *A61B 17/22012* (2013.01); *A61B 2034/102* (2016.02); *A61B 2034/107* (2016.02)

(58) Field of Classification Search
CPC ............ A61B 5/7435; A61B 17/22004; A61B 17/22012; A61B 34/10; A61B 2034/102; A61B 2034/107; A61B 2505/05; G06T 3/20; G06T 3/60; G06T 7/60; G06T 11/00; G06T 11/60; G06T 15/00; G06T 17/00; G06T 17/50; G06T 17/5009; G06T 19/00; G06T 19/20; G06T 19/30; G06T 2200/24; G06T 2207/20092; G06T 2207/30008; G06T 2210/41; G06T 2219/2004; G06T 2219/2016; G06F 17/50; G06F 17/5009; G06F 19/30; G06F 3/011; G06F 3/014; G06F 3/0346; G06F 3/04815; G06F 3/04817; G06F 3/0482; G16H 30/40
USPC .......................................................... 345/419
See application file for complete search history.

(56) References Cited

U.S. PATENT DOCUMENTS

| | | |
|---|---|---|
| 2003/0091967 A1 | 5/2003 | Chosack et al. |
| 2006/0020204 A1* | 1/2006 | Serra .................... A61B 8/0833 600/437 |
| 2006/0177133 A1 | 8/2006 | Kee |
| 2008/0278484 A1* | 11/2008 | Payandeh ............... G06T 17/20 345/419 |
| 2010/0157041 A1 | 6/2010 | Klaiman et al. |
| 2011/0134113 A1* | 6/2011 | Ma ....................... A61B 8/4245 345/419 |
| 2012/0290976 A1* | 11/2012 | Lahm ..................... G06T 19/00 715/810 |
| 2013/0135287 A1* | 5/2013 | McCabe ................ A61B 6/466 345/419 |
| 2013/0316318 A1* | 11/2013 | Frank .................... G09B 23/28 434/262 |
| 2014/0180290 A1* | 6/2014 | Otto ....................... A61B 17/15 606/80 |
| 2016/0374762 A1* | 12/2016 | Case ..................... A61B 8/565 600/424 |

* cited by examiner

METHOD AND SYSTEM FOR INTERACTIVE 3D SCOPE PLACEMENT AND MEASUREMENTS FOR KIDNEY STONE REMOVAL PROCEDURE

CROSS-REFERENCE TO RELATED APPLICATIONS

The present application claims priority to U.S. Provisional Application Ser. No. 62/183,998, filed Jun. 24, 2015, entitled "Method and System for Interactive 3D Scope Placement and Measurements for Kidney Stone Removal Procedure," which is incorporated herein by reference in its entirety.

BACKGROUND

1. Technical Field

The present teaching relates to medical image processing. More specifically, the present teaching is pertaining to interactive medical image processing for planning a surgical procedure, e.g. a kidney stone removal procedure.

2. Description of Related Art

Lithotripsy is a medical procedure used to treat kidney stones. It uses high-energy sound shock waves to break stones apart. Usually when stones are small, a procedure called extracorporeal shock wave lithotripsy (ESWL) is sufficed to break the stones without the need of going through body. However, when stones are quite large (more than 2 cm) or in a location that does not allow effective extracorporeal lithotripsy, an intracorporeal technique called percutaneous ultrasonic lithotripsy may be used. In this method, the surgeon makes a small incision in the back of a patient and creates a tunnel directly into the kidney. A device called nephroscope is inserted into renal pelvis, and ultrasound waves are used to fragment stones. The fragments then are removed through the nephroscope.

A percutaneous ultrasonic lithotripsy procedure requires careful planning to locate the best insertion angle and entry point of the nephroscope. Currently, most of the clinical practices use 2D cross-sectional slices from CT to find the potential treatment areas. This is quite inefficient because users cannot intuitively see the full picture and the 3D spatial relationships among the anatomic structures. Instead, they need to mentally visualize the full area and determine where to insert the scope and how to reach the target area based on their medical training and experiences.

Some anatomic measurements around the renal pelvis are critical to decide the feasibility and effectiveness of the procedure. Infundibulo-pelvic Angle (IPA), infundibular Width (IW), Infundibular Length (IL), Infundibular height (IH), Inter-Calyx angles (ICA) are some of these measurements that are important for the physicians performing lithotripsy. Currently, they are mostly measured in a 2D slice view. This has some drawbacks. First, a physician needs to find a proper slice that can reveal the area that he or she can do the measurement. Second, the slice may not reflect a best angle to do the desired measurement.

Therefore, there is a need for a solution which can be used to perform interactive medical image processing for surgical procedure planning, medical research, or medical education, without the above mentioned drawbacks.

SUMMARY

The present teaching relates to medical image processing. More specifically, the present teaching is pertaining to interactive medical image processing for planning a surgical procedure, e.g. a kidney stone removal procedure.

In one example, a method, implemented on a computing device having at least one processor, storage, and a communication platform capable of connecting to a network for determining one or more measurements related to a kidney is disclosed. A three dimensional (3D) image of the kidney is obtained. The three dimensional image is rendered on a display screen. An input is received from a user specifying a location with respect to a representation of the kidney in the rendered three dimensional image. A representation of an instrument is rendered on the display screen based on the location. The instrument is automatically aligned with an infundibulum pathway of calyx at the location with respect to the kidney. A graphical line extension is rendered on the display screen to visualize the alignment of the instrument. One or more measurements related to the kidney are determined based on the location and an anatomical structure of the kidney.

In a different example, a system, having at least one processor, storage, and a communication platform capable of connecting to a network for determining one or more measurements related to a kidney, is disclosed. The system includes: a 3D object manager configured for obtaining a three dimensional (3D) image of the kidney; a 3D scene renderer configured for rendering the three dimensional image on a display screen; a GUI controller configured for receiving, from a user, an input specifying a location with respect to a representation of the kidney in the rendered three dimensional image; an instrument representation renderer configured for: rendering a representation of an instrument on the display screen based on the location, automatically aligning the instrument with an infundibulum pathway of calyx at the location with respect to the kidney, and rendering a graphical line extension on the display screen to visualize the alignment of the instrument; and an anatomic parameter measurer configured for determining one or more measurements related to the kidney based on the location and an anatomical structure of the kidney.

Other concepts relate to software for implementing the present teaching on medical image processing. A software product, in accord with this concept, includes at least one non-transitory machine-readable medium and information carried by the medium. The information carried by the medium may be executable program code data, parameters in association with the executable program code, and/or information related to a user, a request, content, or information related to a social group, etc.

In one example, a non-transitory and tangible machine readable medium having information recorded thereon for determining one or more measurements related to a kidney is disclosed. The recorded information, when read by the machine, causes the machine to perform a series of processes. A three dimensional (3D) image of the kidney is obtained. The three dimensional image is rendered on a display screen. An input is received from a user specifying a location with respect to a representation of the kidney in the rendered three dimensional image. A representation of an instrument is rendered on the display screen based on the location. The instrument is automatically aligned with an infundibulum pathway of calyx at the location with respect to the kidney. A graphical line extension is rendered on the display screen to visualize the alignment of the instrument. One or more measurements related to the kidney are determined based on the location and an anatomical structure of the kidney.

Additional features will be set forth in part in the description which follows, and in part will become apparent to those skilled in the art upon examination of the following and the accompanying drawings or may be learned by production or operation of the examples. The features of the present teachings may be realized and attained by practice or use of various aspects of the methodologies, instrumentalities and combinations set forth in the detailed examples discussed below.

BRIEF DESCRIPTION OF THE DRAWINGS

The present teaching claimed and/or described herein is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, systems, components, and/or circuitry have been described at a relatively high-level, without detail, in order to avoid unnecessarily obscuring aspects of the present teachings.

To overcome the aforementioned inefficiency and shortcomings in existing techniques, a planning tool is designed in the present teaching for user to interactively place a nephroscope and perform key measurements. This tool may allow physicians to perform measurements directly in the same 3D space as the anatomic 3D structures resided in. In this way, users can have a full picture of the whole 3D space, 3D anatomic structures and neighboring structures relationships. They can intuitively do the measurements with confidence and accuracy. This tool can also allow physicians to interactively place and adjust a 3D virtual probe as a nephroscope in the 3D space.

The present teaching relates to interactive 3D scope placement and measurements related to an organ, e.g. a kidney. The present teaching may provide methods of image processing for kidney stone removal procedure. The method and system disclosed in the present teaching can be used in pre-surgical planning for either extracorporeal or intracorporeal lithotripsy to help physicians decide the effectiveness of treatment and route of invasive procedure. The method and system disclosed in the present teaching can provide direct interaction schemes in 3D space to place and adjust nephroscope. The method and system disclosed in the present teaching can also provide direct measurements in 3D space for various surgical significant measurements. It can be understood that, in accordance with various embodiments, the medical image processing disclosed in the present teaching may be implemented not only for surgical procedure planning, but also for medical research and/or medical education.

Figure 1:
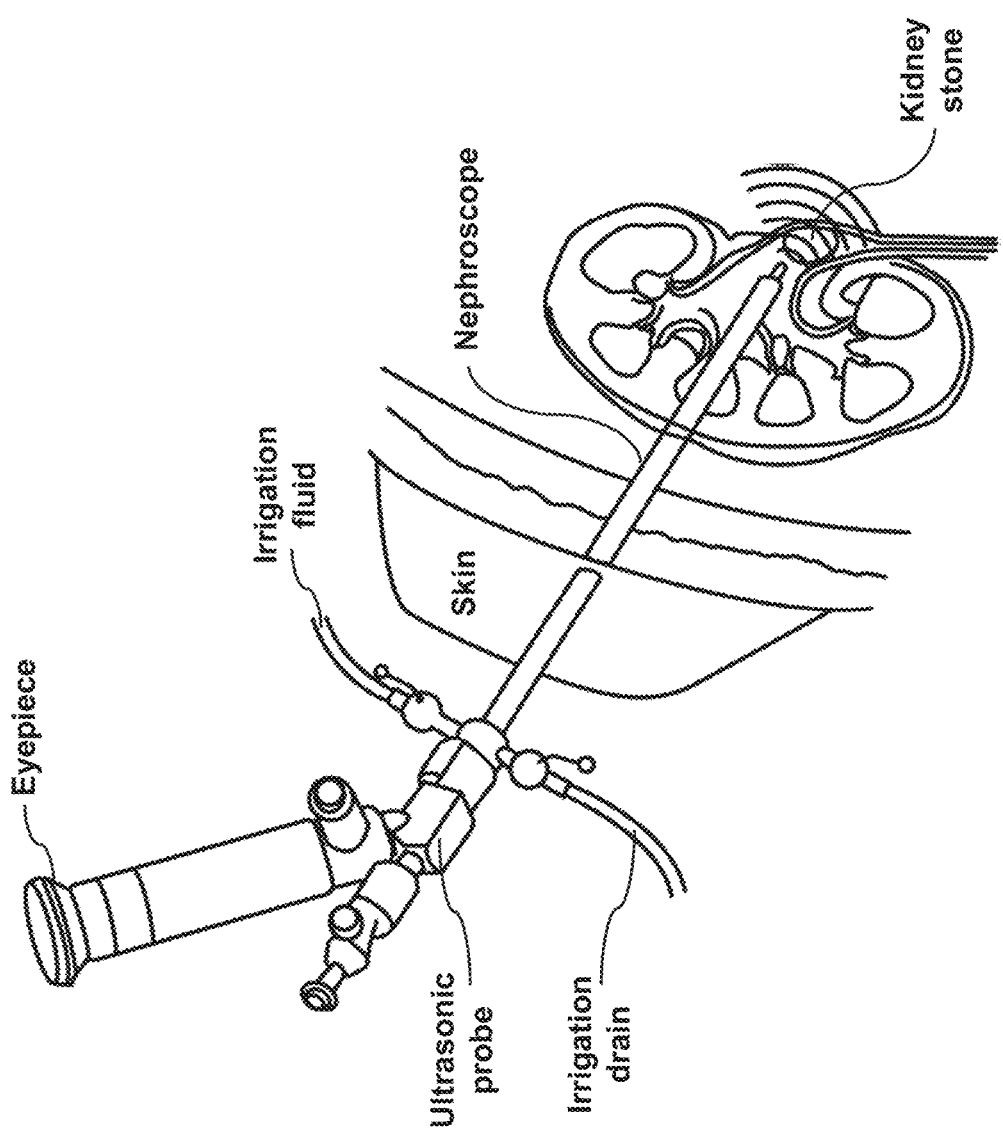
FIG. 1 depicts an exemplary percutaneous ultrasound lithotripsy, according to an embodiment of the present teaching.
Figure 2:
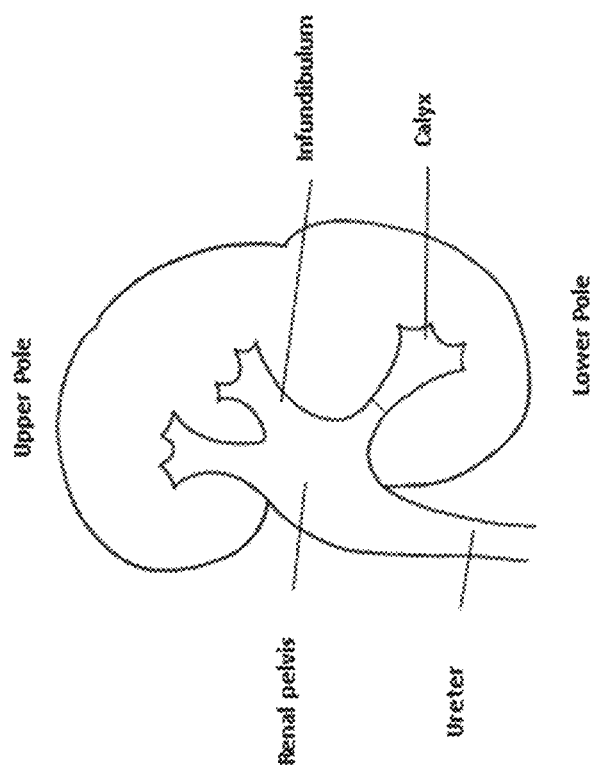
FIG. 2 shows some exemplary anatomic terms around the kidney related to lithotripsy procedure, according to an embodiment of the present teaching.

The pre-assumption is that there is a virtual 3D spatial space already exists (such as in U.S. Pat. No. 7,315,304B2) and meaningful urological anatomic structures such as kidney, ureter, renal pelvis, and calyces are already segmented from a scanned medical data and placed inside this 3D space. This virtual 3D scene is displayed on a 2D screen of a computer monitor. The interaction or manipulation is happening inside this virtual 3D space with user's input from 2D computer mouse or keyboard converted into 3D actions applied to the objects inside the 3D virtual space. FIG. 1 depicts an exemplary percutaneous ultrasound lithotripsy, according to an embodiment of the present teaching. FIG. 2 shows some exemplary anatomic terms around the kidney related to lithotripsy procedure, according to an embodiment of the present teaching.

There are some general 3D visualization workstations or software packages that let users prepare and visualize some 3D structures. However, none of them is tailored to percutaneous ultrasonic lithotripsy procedure which may make it hard or even impossible to use.

Figure 3:
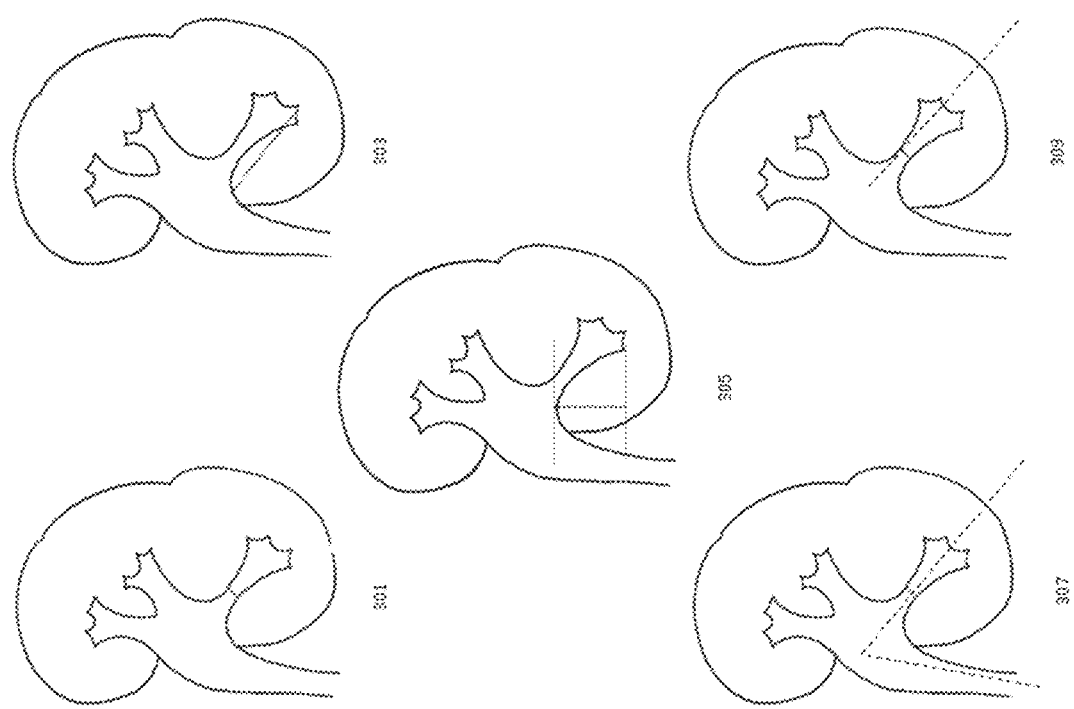
FIG. 3 shows some exemplary graphical definitions of various infundibulum related measurements, according to an embodiment of the present teaching.

FIG. 3 shows graphical definitions of various infundibulum related measurements in renal pelvis. Infundibular width (IW) 301 is measured as the narrowest point in the axis of the lower infundibulum. Infundibular length (IL) 303 is measured as the distance between the most distal point of the calyx containing the calculus and the midpoint of the lower lip of the renal pelvis. Infundibular height (IH) 305 measured as the distance between the horizontal line passing through the lowermost part of the calyx containing the calculus and the highest point of the lower lip of the renal pelvis. Infundibulo-pelvic Angle (IPA) 307 is measured as the angle of the lower infundibulum and ureter in the renal pelvis area. Inter-calyx Angle (ICA) 309 is measured as the angle of two calyces.

Figure 4A:
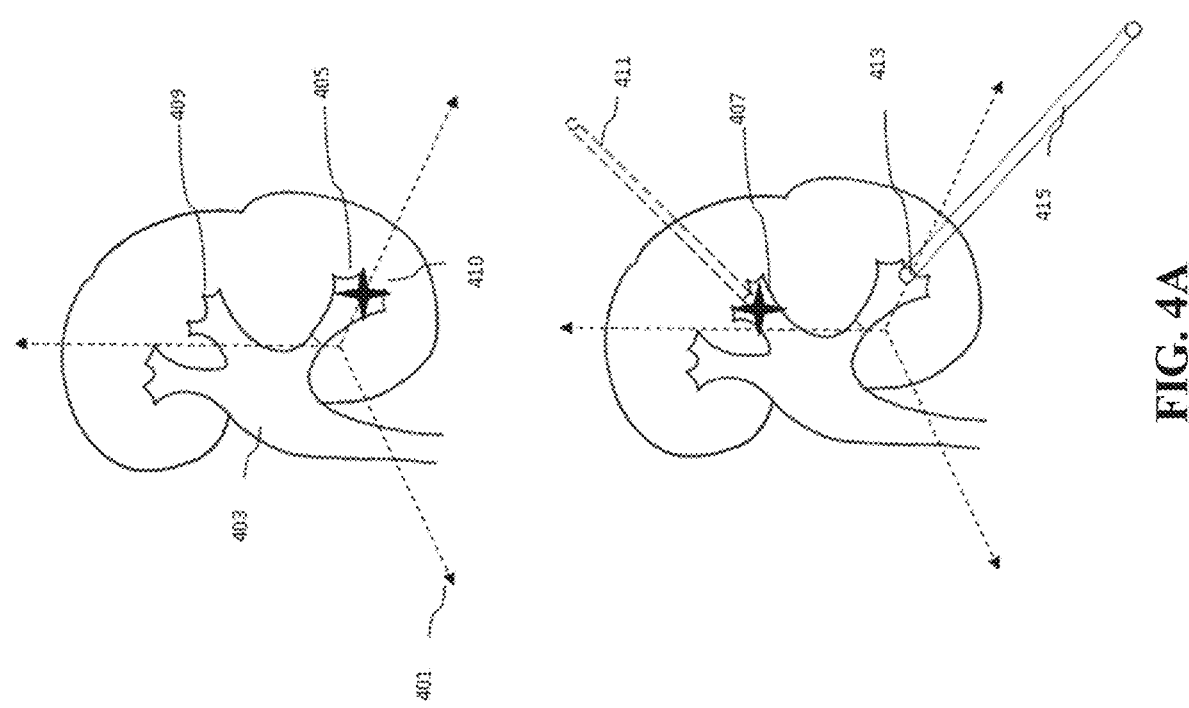
FIGS. 4A and 4B shows an exemplary operation of interactively placing a 3D virtual nephroscope, according to an embodiment of the present teaching.
Figure 4B:
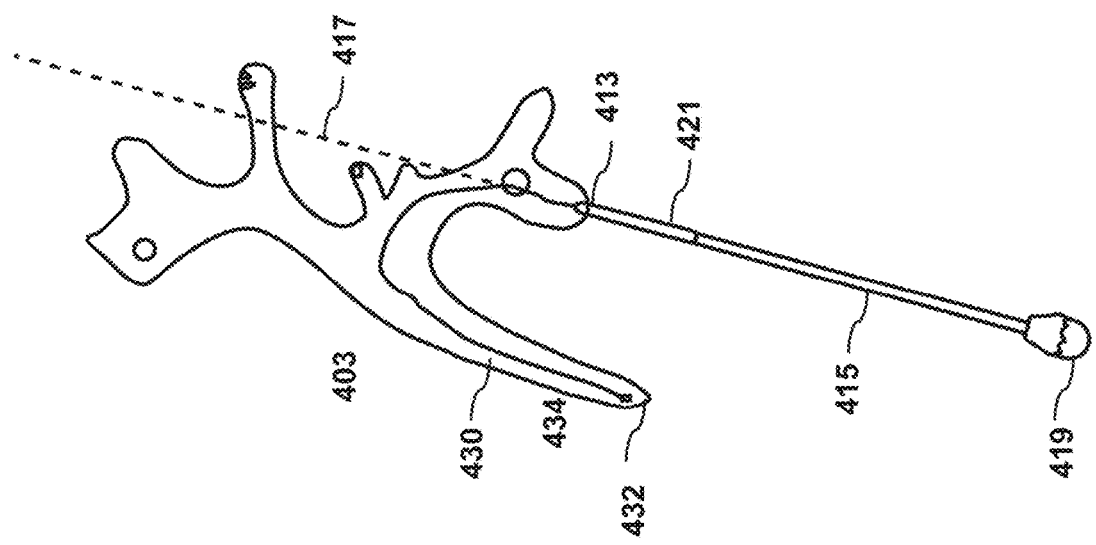

FIGS. 4A and 4B shows the operation of interactively placing a 3D virtual nephroscope. A segmented 3D urological structure 403 is resided in a 3D space 401. A user uses a computer mouse to click a spot 410 in the 3D space near a calyx of interest 405. A virtual nephroscope 415 is displayed in the 3D space. The scope tip 413 is placed at the location of the calyx 405. This operation is rendered more realistically in FIG. 4B. We provide an automatic alignment feature to avoid tedious manual alignment. The system automatically aligns the scope 415 with the infundibulum pathway of the calyx of interest 405. A graphical line extension 417 is displayed to help user visualize the alignment. This alignment can be finely tuned interactively by the user using the orientation control 419 of the scope. The tip 413 location can also be adjusted by the user using the forward/backward control 421. The system also automatically computes a central curve 430 that connects the tip 413 of the nephroscope and a point 432 in the ureter 434. The central curve 430 goes through the urological structure 403. This central curve 430 will be used in the subsequent measuring operations.

With this interactive tool, users can easily place nephroscope to a different calyx and do the measurements to determine the best calyx to perform lithotripsy. For example, if the user clicks another spot 407 near a different calyx 409, a virtual nephroscope 411 may be placed and aligned with the infundibulum pathway of the different calyx 409.

Figure 5:
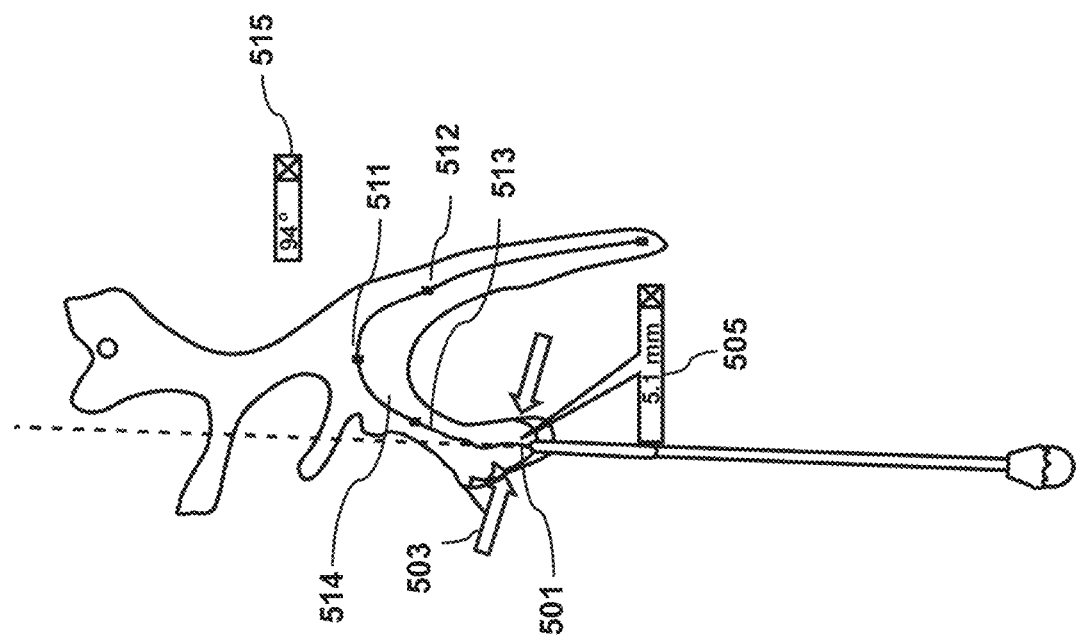
FIG. 5 shows exemplary IPA measurement and IW measurement, according to an embodiment of the present teaching.

FIG. 5 depicts how to perform measurements of IW and IPA. For IW measurement, Users can use mouse to click on a spot 501 of the narrow passage of a calyx to get a measurement of the IW. A graphical indicator 503 of IW measurement is shown in the 3D space with respect to the 3D structure. The numerical value 505 of the IW measurement is shown also within the 3D view as a graphical overlay. For IPA measurement, users can click on three points 511, 512, 513 along the central curve 430 the system provided to define the angle 514 in 3D. The numerical value 515 of the angle is shown overlaid in the 3D scene. Since these measurements are displayed in 3D, users can rotate the scene and see these 3D measurements in different viewing angle.

Figure 6:
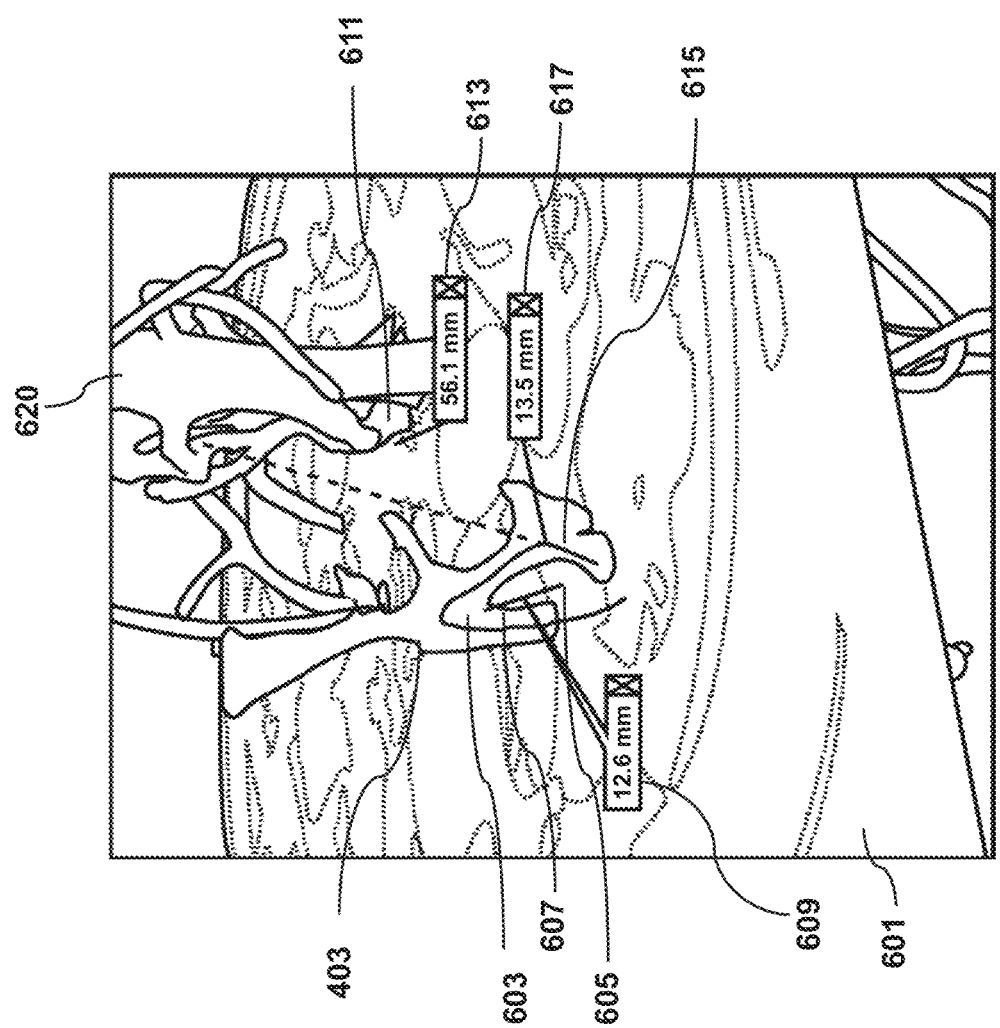
FIG. 6 shows exemplary IH measurement and other measurements, according to an embodiment of the present teaching.

FIG. 6 depicts how to perform measurements of IH and other kinds of measurements. For IH measurement, it requires a point in urological structure 403 and a point in a 3D space without cling to any 3D structure. In our 3D scene, users can immerge a slice 601 in the 3D space, scroll the slice to be in the lowermost part of calyx, click one point 605 on the slice that is exactly below the highest point of the lower lip of the renal pelvis and click the highest point 603 to define a straight line 607 distance as IH. Its numerical value is shown and overlaid within the 3D scene view 609. We can also perform a general straight distance measurement such as we pick one point in urological structure 403 and a neighboring anatomic structure 620 to get a measurement 611 and its numerical value overlaid 613. This kind of measurement can be used to do IL measurement by clicking one point on the tip of calyx and one point at the midpoint of the lower lip of the renal pelvis. We can click two points along the central curve 430 to obtain the curve distance 615 along the central curve and its numerical value overlaid 617. This is useful in determining the distance required to maneuver the scope within the renal pelvis.

Figure 7:
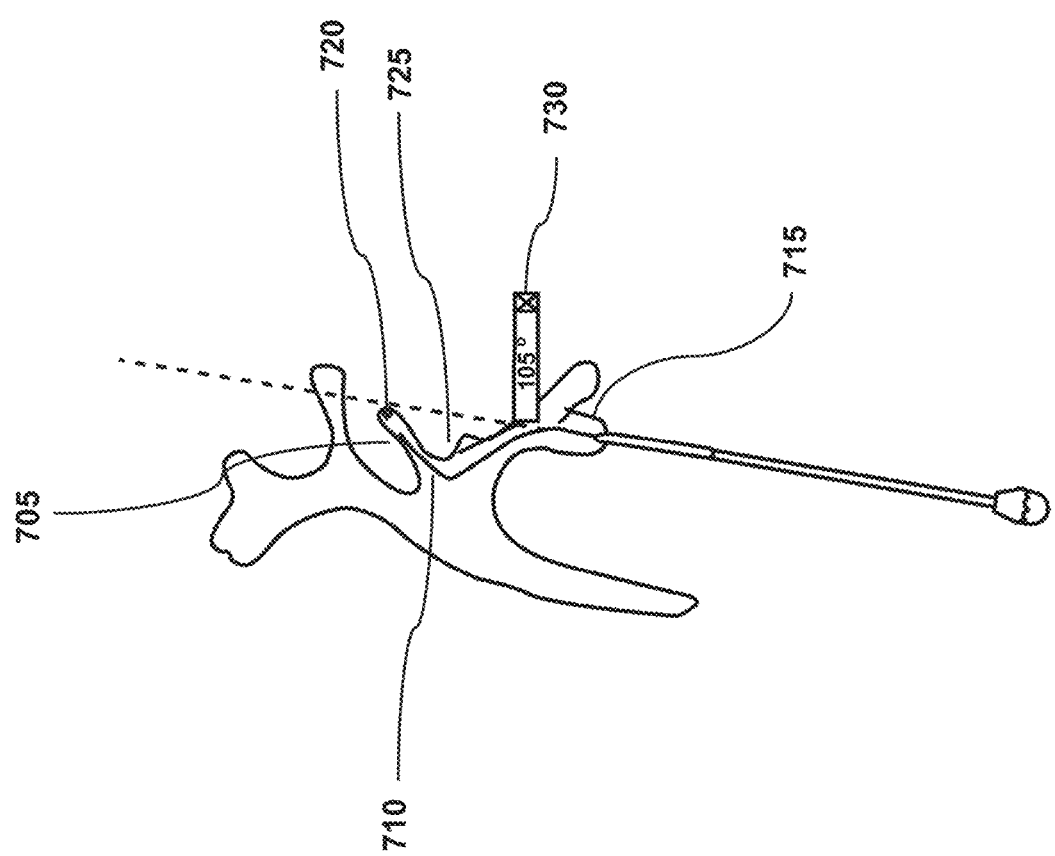
FIG. 7 shows exemplary ICA measurement, according to an embodiment of the present teaching.

FIG. 7 depicts how to perform measurements of ICA. Once the calyx of nephroscope is determined, users can click on another calyx 705 to make the system generate a central curve 710 from the tip 715 of nephroscope to the tip 720 of the newly-clicked calyx. The ICA angle 725 can be obtained by clicking three points along the central curve similar to IPA described above. The numerical value 730 is similarly overlaid in the 3D scene.

The measurements are used for surgical planning of a kidney stone removal procedure. For example, IPA affects the effectiveness of the treatment of ESWL. An acute IPA of the lower pole hinders the spontaneous passage of fragments after ESWL and the clearance of lower pole stone treated with SWL.

Some combinations of the measurements can be used by medical practices to predict or indicate the effectiveness of SWL treatment. So to provide all the possible measurements easily and intuitively by the present teaching is also an important feature for doctors to determine their treatment.

Figure 8:
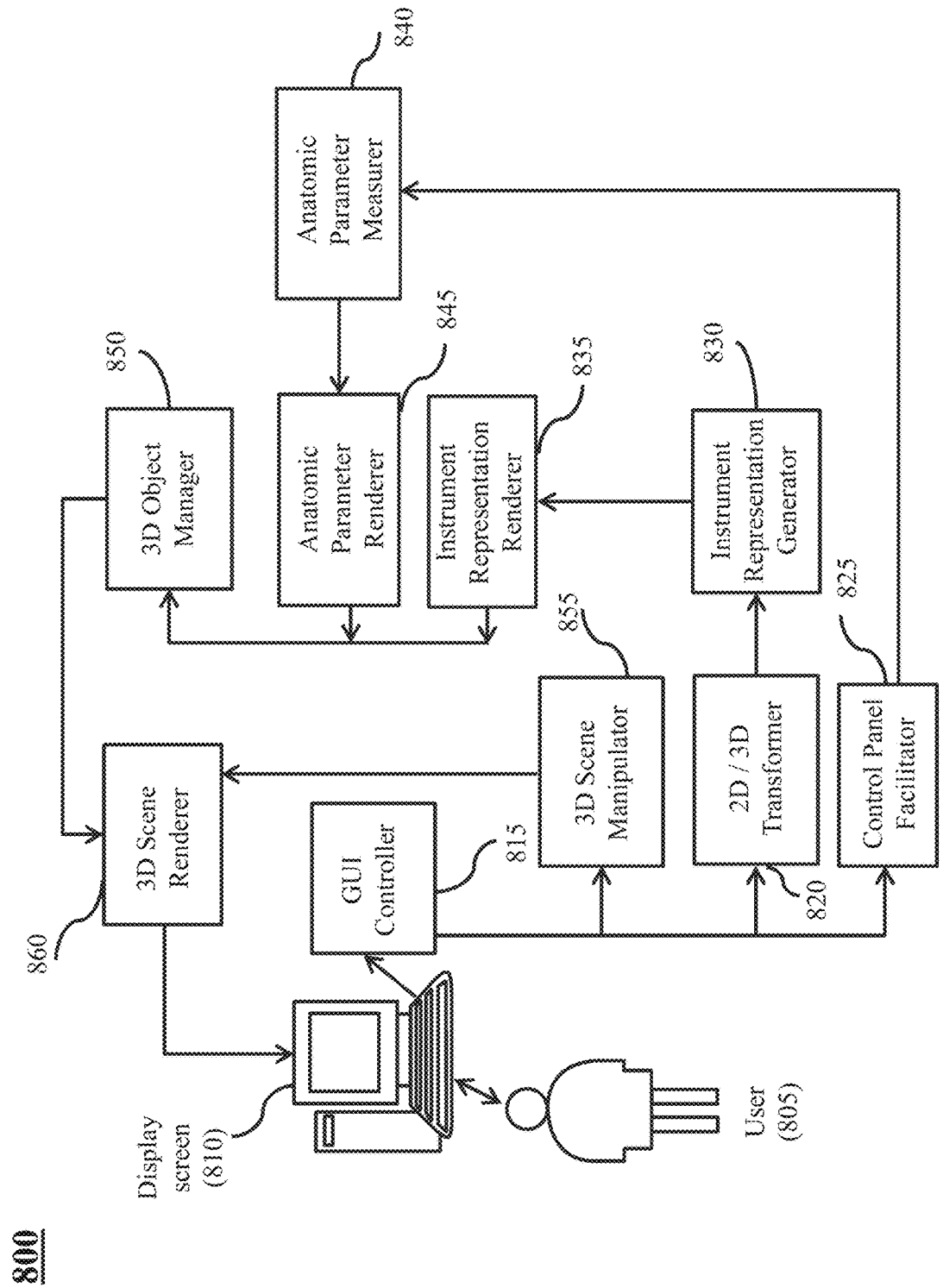
FIG. 8 depicts an exemplary construct of a system that facilitates interactive 3D scope placement and measurements related to a kidney, according to an embodiment of the present teaching.

FIG. 8 depicts an exemplary construct of a system 800 that facilitates interactive 3D scope placement and measurements related to a kidney, according to an embodiment of the present teaching. The system 800 comprises a display device 810, a graphical user interface (GUI) controller 815, a 2D/3D transformer 820, an instrument representation generator 830, a control panel facilitator 825, an instrument representation renderer 835, an anatomic parameter measurer 840, an anatomic parameter renderer 845, a 3D object manager 850, a 3D scene manipulator 855, and a 3D scene renderer 860.

A user 805 may interact with the system 800 via a user interface displayed on the display device 810. The GUI controller 815 may control interaction between the system 800 and user 805. If the user 805 desires to use a tool associated with a virtual probe once a 3D scene is set up, the user may request the system to retrieve 3D object information from the 3D object manager 850 and render such objects via the 3D scene renderer 860. When such user request is entered via the user interface, the GUI controller 815 may then interpret the request and accordingly activate appropriate functional modules to perform the requested operations.

For example, if the request is to change the orientation of the 3D scene, the system may activate the 3D scene manipulator 855 to modify the orientation of the 3D scene based on the specification from the user. During this process, the user and the GUI controller may continuously interact, e.g., user may click a point in the 3D scene and drag along a certain direction so that the entire 3D scene may move along in the same direction. Similarly, the user may exercise the same control with respect to a particular 3D object such as a virtual probe.

A user may also interact with the system to exercise various controls over a probe. When the user manually controls a probe via a 2D display screen, the 2D/3D transformer 820 can dynamically transform a 2D screen point to a 3D point in the 3D scene, and then pass the 3D point to the instrument representation generator 830 which can generate a representation of an instrument. The representation of an instrument may be a 3D virtual probe representing a scope, e.g. a nephroscope. The virtual probe may be then rendered in the 3D scene by the instrument representation renderer 835.

As discussed herein, the system can also provide the means for a user to exercise various control regarding the operation of the system. For example, via the control panel facilitator 825, a user may activate or deactivate various infundibulum related measurements performed at 840. The results of these measurements may be then rendered in the 3D scene by the anatomic parameter renderer 845.

A user may also set desired mode of display which may also be personalized and such a setting may be applied automatically when the user signs up with the system. For example, a user may desire to always have the skin (a 3D object) displayed in a transparent mode.

Figure 9:
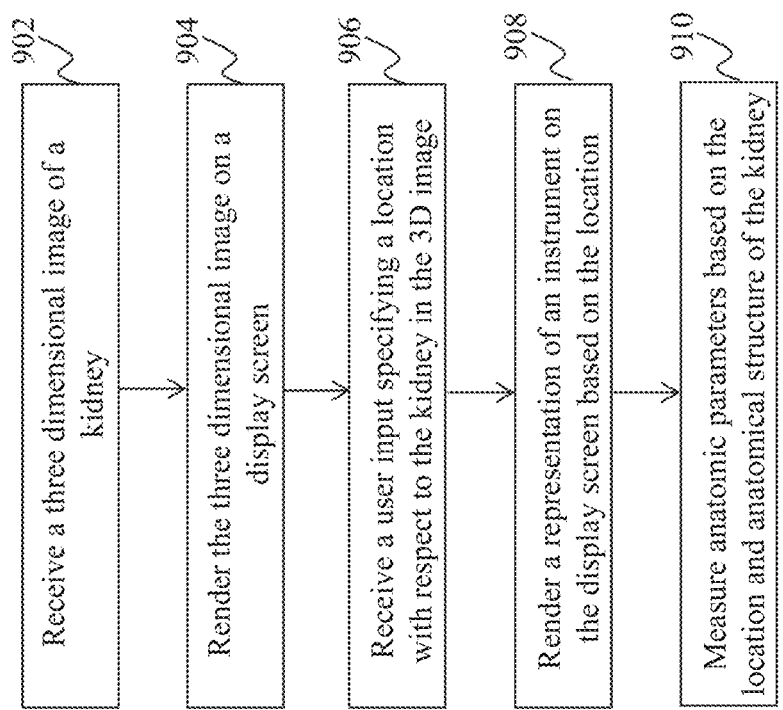
FIG. 9 is a flowchart of an exemplary process performed by the system in FIG. 8, according to an embodiment of the present teaching.

FIG. 9 is a flowchart of an exemplary process performed by the system 800 in FIG. 8, according to an embodiment of the present teaching. A three dimensional image of a kidney is received or obtained at 902. The three dimensional image is rendered at 904 on a display screen. A user input is received at 906, specifying a location with respect to the kidney in the 3D image. At 908, a representation of an instrument is rendered on the display screen based on the location. At 910, one or more anatomic parameters are measured based on the location and anatomical structure of the kidney. The anatomic parameters may include one or more infundibulum related measurements as shown FIG. 3.

Figure 10:
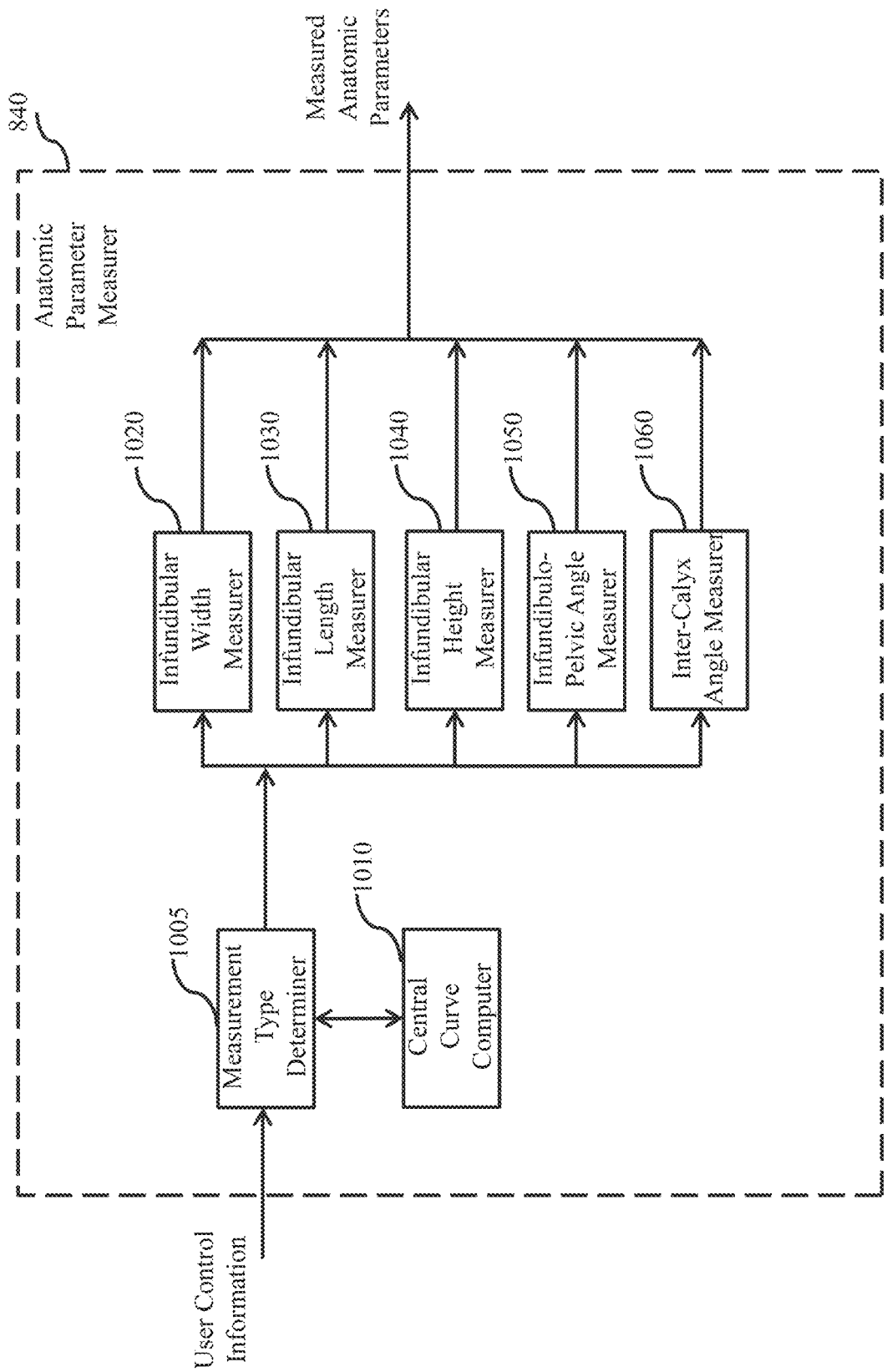
FIG. 10 depicts an exemplary construct of an anatomic parameter measurer, according to an embodiment of the present teaching.

FIG. 10 depicts an exemplary construct of an anatomic parameter measurer 840, according to an embodiment of the present teaching. The anatomic parameter measurer 840 in this example includes a measurement type determiner 1005, a central curve computer 1010, an infundibular width measurer 1020, an infundibular length measurer 1030, an infundibular height measurer 1040, an infundibulo-pelvic angle measurer 1050, and an inter-calyx angle measurer 1060.

The measurement type determiner 1005 in this example can receive user control information from the control panel facilitator 825 and determine the type of measurement requested by the user. Based on the determination result, the measurement type determiner 1005 can send instructions to one or more corresponding measurers shown in FIG. 10. In one embodiment, the measurement type determiner 1005 may also send an instruction to the central curve computer 1010 for computing a central curve, based on control information from the user.

The central curve computer 1010 in this example can compute a central curve, e.g. the central curve 430 that connects the tip 413 of the nephroscope and a point 432 in the ureter 434. As shown in FIG. 4, the central curve 430 goes through the urological structure 403 and may be used in the subsequent measuring operations. This computation of central curve can be automatically performed by the measurement type determiner 1005, or upon a request from the user.

The infundibular width measurer 1020 and the infundibulo-pelvic angle measurer 1050 in this example can perform measurements of IW and IPA, respectively, as shown in FIG. 5. The infundibular length measurer 1030 and the infundibular height measurer 1040 in this example can perform measurements of IL and IW, respectively, as shown in FIG. 6. The inter-calyx angle measurer 1060 in this example can perform measurement of ICA, as shown in FIG. 7.

Figure 11:
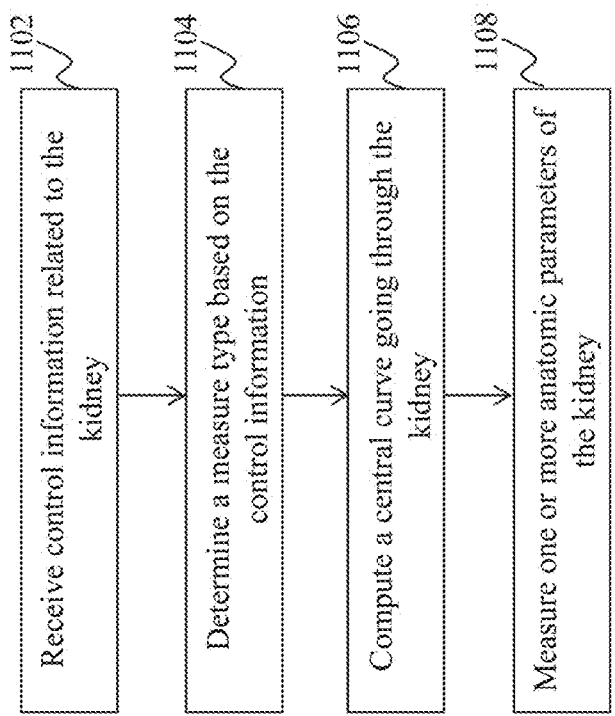
FIG. 11 is a flowchart of an exemplary process performed by an anatomic parameter measurer, according to an embodiment of the present teaching.

FIG. 11 is a flowchart of an exemplary process performed by an anatomic parameter measurer, e.g. the anatomic parameter measurer 840 in FIG. 10, according to an embodiment of the present teaching. At 1102, control information related to the kidney, e.g. a kidney, is received. A measure type is determined at 1104 based on the control information. A central curve going through the kidney may be computed at 1106. At 1108, one or more anatomic parameters of the kidney are measured. For example, the anatomic parameters may include one or more infundibulum related parameters in FIG. 3.

Figure 12:
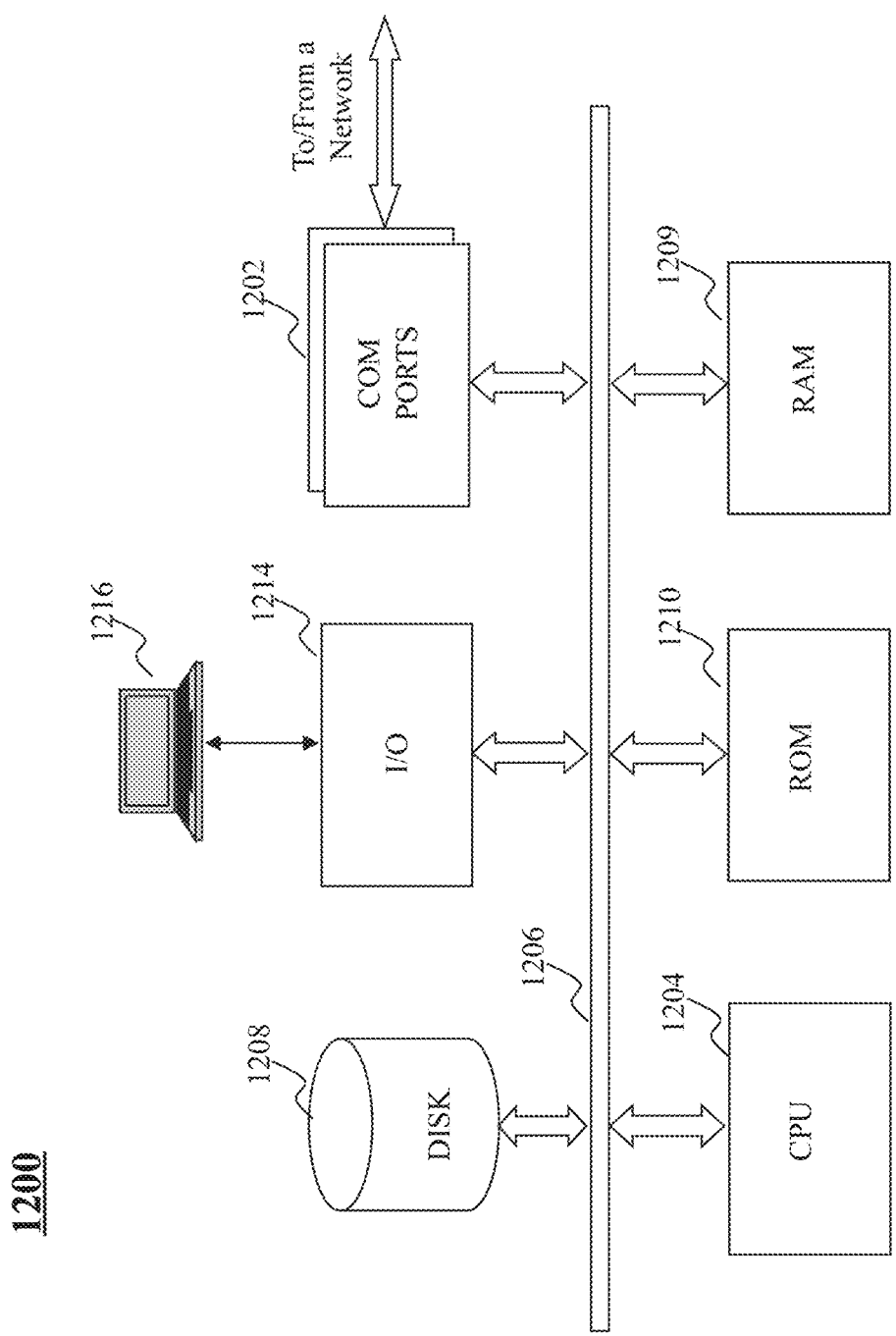
FIG. 12 depicts the architecture of a computer which can be used to implement a specialized system incorporating the present teaching.

FIG. 12 depicts the architecture of a computing device which can be used to realize a specialized system implementing the present teaching. Such a specialized system incorporating the present teaching has a functional block diagram illustration of a hardware platform which includes user interface elements. The computer may be a general purpose computer or a special purpose computer. Both can be used to implement a specialized system for the present teaching. This computer 1200 may be used to implement any component of medical image processing techniques, as described herein. For example, the system 800 may be implemented on a computer such as computer 1200, via its hardware, software program, firmware, or a combination thereof. Although only one such computer is shown, for convenience, the computer functions relating to medical image processing as described herein may be implemented in a distributed fashion on a number of similar platforms, to distribute the processing load.

The computer 1200, for example, includes COM ports 1202 connected to and from a network connected thereto to facilitate data communications. The computer 1200 also includes a central processing unit (CPU) 1204, in the form of one or more processors, for executing program instructions. The exemplary computer platform includes an internal communication bus 1206, program storage and data storage of different forms, e.g., disk 1208, read only memory (ROM) 1210, or random access memory (RAM) 1212, for various data files to be processed and/or communicated by the computer, as well as possibly program instructions to be executed by the CPU 1204. The computer 1200 also includes an I/O component 1214, supporting input/output flows between the computer and other components therein such as user interface elements 1216. The computer 1200 may also receive programming and data via network communications.

Hence, aspects of the methods of medical image processing, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present teachings are amenable to a variety of modifications and/or enhancements. For example, although the implementation of various components described above may be embodied in a hardware device, it may also be implemented as a software only solution—e.g., an installation on an existing server. In addition, the medical image processing system as disclosed herein may be implemented as a firmware, firmware/software combination, firmware/hardware combination, or a hardware/firmware/software combination.

While the foregoing has described what are considered to constitute the present teachings and/or other examples, it is understood that various modifications may be made thereto and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

We claim:

1. A method, implemented on a computing device having at least one processor, storage, and a communication platform capable of connecting to a network for determining one or more measurements related to a kidney, the method comprising:
    obtaining a three dimensional (3D) image of the kidney;
    rendering the three dimensional image in a 3D virtual space;
    receiving an input from a user, the input corresponding to a direct interaction of the user within the 3D virtual space and specifying a location with respect to a representation of the kidney in the rendered three dimensional image;
    rendering a representation of an instrument in the 3D virtual space based on the location;
    automatically aligning in the 3D virtual space, the representation of the instrument with an infundibulum pathway of calyx at the location with respect to the kidney based on the received input from the user;
    rendering a graphical line extension from the representation of the instrument in the 3D virtual space to visualize the alignment of the representation of the instrument; and
    determining the one or more measurements related to the kidney based on the location and an anatomical structure of the kidney.

2. The method of claim 1, wherein the one or more measurements are used for at least one of: surgical planning, research of the kidney, and educational material preparation.

3. The method of claim 1, wherein the instrument is represented by a probe.

4. The method of claim 3, further comprising adjusting the alignment of the probe based on an interaction between the user and the three dimensional image.

5. The method of claim 3, further comprising adjusting the location based on an interaction between the user and the three dimensional image, wherein a tip of the probe is placed at the location.

6. The method of claim 3, further comprising computing a central curve that connects a tip of the probe and a point in the kidney, wherein the central curve goes through an urological structure of the kidney.

7. The method of claim 1, wherein the one or more measurements include at least one of the following:
    an infundibular width of the kidney;
    an infundibular length of the kidney;
    an infundibular height of the kidney;
    an infundibulo-pelvic angle of the kidney; and
    an inter-calyx angle of the kidney.

8. The method of claim 1, further comprising:
    computing a central curve that connects a tip of the instrument and a point in the kidney, wherein the central curve goes through an urological structure of the kidney.

9. A system, having a processor, a storage comprising instructions, and a hardware communication platform capable of connecting to a network for determining one or more measurements related to a kidney, wherein the instructions when executed by the system cause the system to:
    obtain a three dimensional (3D) image of the kidney;
    render the three dimensional image in a 3D virtual space;
    receive an input from a user, the input corresponding to a direct interaction of the user within the 3D virtual space and specifying a location with respect to a representation of the kidney in the rendered three dimensional image;
    render a representation of an instrument in the 3D virtual space based on the location;
    automatically align in the 3D virtual space, the representation of the instrument with an infundibulum pathway of calyx at the location with respect to the kidney based on the received input from the user;
    render a graphical line extension from the representation of the instrument in the 3D virtual space to visualize the alignment of the representation of the instrument; and
    determine the one or more measurements related to the kidney based on the location and an anatomical structure of the kidney.

10. The system of claim 9, wherein the one or more measurements are used for at least one of: surgical planning, research of the kidney, and educational material preparation.

11. The system of claim 9, wherein the instrument is represented by a probe.

12. The system of claim 11, wherein the instructions when executed by the system further cause the system to adjust the alignment of the probe based on an interaction between the user and the three dimensional image.

13. The system of claim 11, wherein the instructions when executed by the system further cause the system to adjust the location based on an interaction between the user and the three dimensional image, wherein a tip of the probe is placed at the location.

14. The system of claim 11, wherein the instructions when executed by the system further cause the system to compute a central curve that connects a tip of the probe and a point in the kidney, wherein the central curve goes through an urological structure of the kidney.

15. The system of claim 9, wherein the one or more measurements include at least one of the following:
   an infundibular width of the kidney;
   an infundibular length of the kidney;
   an infundibular height of the kidney;
   an infundibulo-pelvic angle of the kidney; and
   an inter-calyx angle of the kidney.

16. A non-transitory machine readable medium having information recorded thereon for determining one or more measurements related to a kidney, wherein the information, when read by a machine, causes the machine to perform the following:
   obtaining a three dimensional (3D) image of the kidney;
   rendering the three dimensional image in a 3D virtual space;
   receiving an input from a user, the input corresponding to a direct interaction of the user within the 3D virtual space and specifying a location with respect to a representation of the kidney in the rendered three dimensional image;
   rendering a representation of an instrument in the 3D virtual space based on the location;
   automatically aligning in the 3D virtual space, the representation of the instrument with an infundibulum pathway of calyx at the location with respect to the kidney based on the received input from the user;
   rendering a graphical line extension from the representation of the instrument in the 3D virtual space to visualize the alignment of the representation of the instrument; and
   determining the one or more measurements related to the kidney based on the location and an anatomical structure of the kidney.

17. The medium of claim 16, wherein the one or more measurements are used for at least one of: surgical planning, research of the kidney, and educational material preparation.

18. The medium of claim 16, wherein the instrument is represented by a probe.

19. The medium of claim 18, wherein the information, when read by a machine, further causes the machine to perform the following: adjusting the alignment of the probe based on an interaction between the user and the three dimensional image.

20. The medium of claim 18, wherein the information, when read by a machine, further causes the machine to perform the following: adjusting the location based on an interaction between the user and the three dimensional image, wherein a tip of the probe is placed at the location.

21. The medium of claim 18, wherein the information, when read by a machine, further causes the machine to perform the following: computing a central curve that connects a tip of the probe and a point in the kidney, wherein the central curve goes through an urological structure of the kidney.

22. The medium of claim 16, wherein the one or more measurements include at least one of the following:
   an infundibular width of the kidney;
   an infundibular length of the kidney;
   an infundibular height of the kidney;
   an infundibulo-pelvic angle of the kidney; and
   an inter-calyx angle of the kidney.

* * * * *